United States Patent
Shchervinsky

(10) Patent No.: US 6,866,657 B2
(45) Date of Patent: Mar. 15, 2005

(54) DRAIN CATHETERS

(76) Inventor: Semyon Shchervinsky, 6 Menlo Dr., Whitehouse Station, NJ (US) 08889

(*) Notice: Subject to any disclaimer, the term of this patent is extended or adjusted under 35 U.S.C. 154(b) by 175 days.

(21) Appl. No.: 10/189,216

(22) Filed: Jul. 4, 2002

(65) Prior Publication Data

US 2004/0006331 A1 Jan. 8, 2004

(51) Int. Cl.$^7$ .......................... A61M 25/00; A61M 1/00
(52) U.S. Cl. ........................................ 604/266; 604/543
(58) Field of Search ................................ 604/540–544, 604/266, 164.01, 35

(56) References Cited

U.S. PATENT DOCUMENTS

| | | | |
|---|---|---|---|
| 3,136,316 A | | 6/1964 | Beall |
| 3,407,817 A | | 10/1968 | Galleher, Jr. |
| 3,590,820 A | | 7/1971 | Nehra et al. |
| 3,599,641 A | | 8/1971 | Sheridan |
| 3,630,206 A | | 12/1971 | Gingold |
| 3,860,008 A | | 1/1975 | Miner et al. |
| 4,398,910 A | * | 8/1983 | Blake et al. ............... 604/266 |
| 4,445,897 A | | 5/1984 | Ekbladh et al. |
| 4,465,481 A | | 8/1984 | Blake |
| 5,346,467 A | * | 9/1994 | Coll ............................. 604/8 |
| 5,360,414 A | * | 11/1994 | Yarger ....................... 604/264 |
| 5,549,579 A | | 8/1996 | Batdorf et al. |
| 6,099,513 A | | 8/2000 | Spehalski |
| 2004/0006311 A1 | * | 1/2004 | Shchervinsky ......... 604/164.01 |

* cited by examiner

*Primary Examiner*—Larry I. Schwartz
*Assistant Examiner*—Michael G. Bogart

(57) ABSTRACT

The present invention is directed to a wound drain catheter for draining fluid from, or supplying medication to, a wound in a patient. The wound drain catheter comprises a drain, a flexible outflow tube, and means for connecting the drain to the flexible outflow tube. The drain comprises a hollow core having a longitudinal axis; plural struts extending outwardly from the hollow core and being closed to the hollow core; and plural overhangs connected to the outward ends of the struts, respectively, the overhangs cooperating with the struts to form plural longitudinal lumens, the overhangs cooperating with each other to form, on the outer surface of the drain, segments of a segmented, closed curve with gaps between the segments providing plural longitudinal grooves for fluid communication between the wound and a respective lumen, the grooves sized to inhibit tissue from growing therein and debris from passing therethrough. The present invention also includes a method for draining fluid from, or supplying medication to, a wound in a patient.

20 Claims, 8 Drawing Sheets

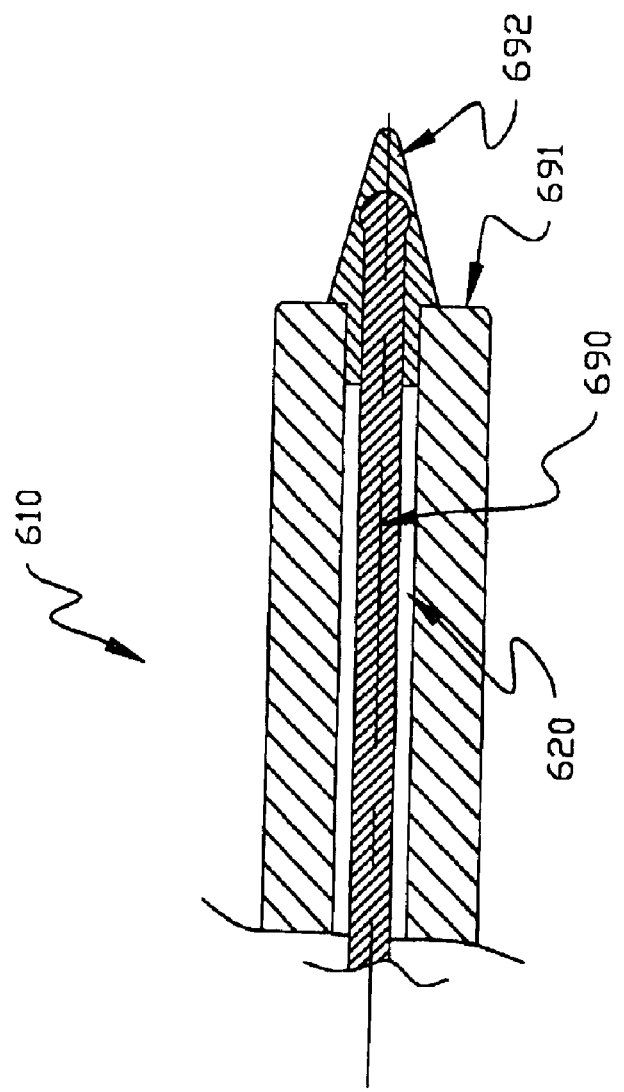
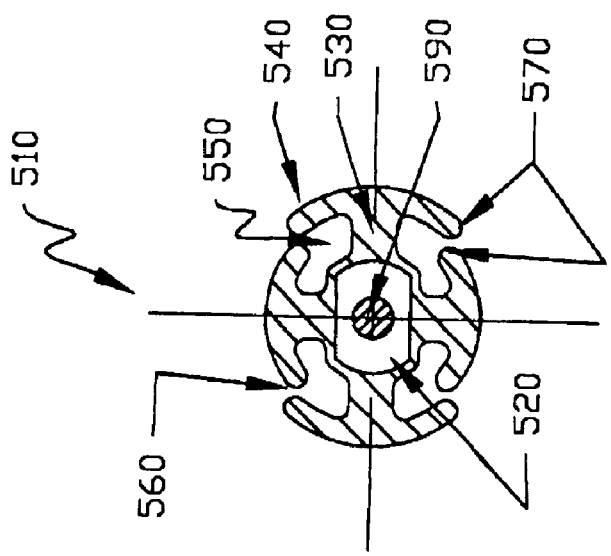
FIG. 6
FIG. 5

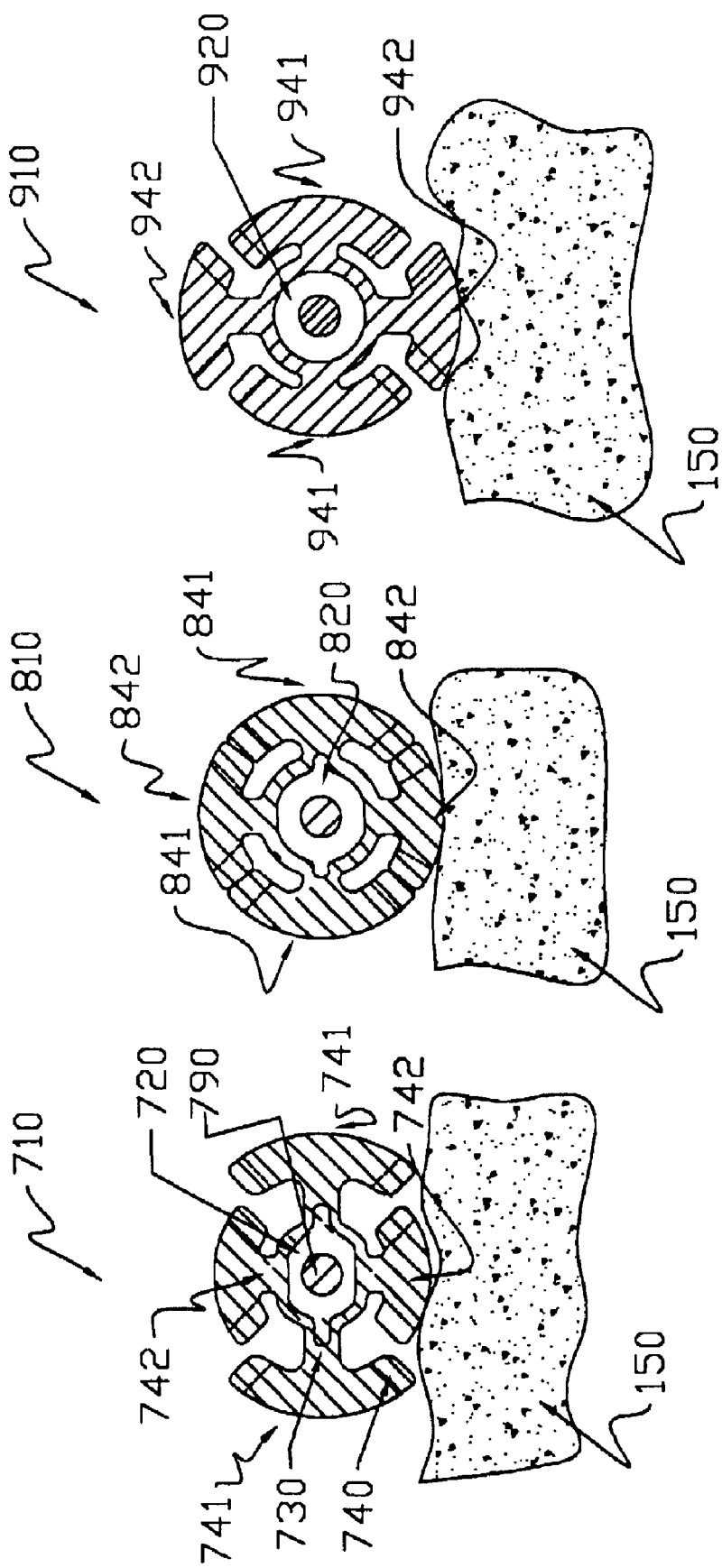

DRAIN CATHETERS

FIELD OF THE INVENTION

The present invention relates to multilumen wound drain catheters for removing fluids from a wound. The wound drain catheters may also be used to supply medication to a wound.

DESCRIPTION OF THE BACKGROUND

Wound drain catheters for draining closed wounds generally comprise a drain portion in fluid communication with a wound and an outflow tube for transporting fluid from the drain to a reservoir. Typically, the outflow tube is connected to a vacuum source after the drain has been placed in the wound and the wound has been closed. The most common type of wound drain catheter is a tubing perforated with spaced apertures through the tubing wall. The spaced apertures are usually in opposed pairs and the spacing between the aperture pairs may vary. A significant problem with wound drain catheters is that wound debris, such as clots, may block the apertures thereby reducing the effectiveness of the drain. Another problem is that as the wound heals, tissue tends to form in the apertures of the wound drain catheter further reducing the effectiveness of the drain. In addition, when the wound drain catheter is removed from the patient, such as by applying a pulling force, any tissue that has grown into the apertures will be torn from the patient's body causing discomfort and retarding the healing process. If tissue growth into the apertures is extensive, the drain may break during removal thereby leaving a portion of the drain in the patient's body requiring additional surgery.

Other wound drain catheters have flat or round elongated channel shapes with a solid core, however, these channels tend to become easily clogged. Furthermore, when these drain catheters are removed such as by pulling, the diameter of the catheter decreases and gaps between channels causes pinching thereby trapping tissue during drain removal.

U.S. Pat. No. 3,136,316 (Beal) discloses a catheter comprising a tubular body having a longitudinally extending passage. A distal marginal end of the tubular body has at least two longitudinally extending grooves. At least one aperture provides communication between the passage and each of the longitudinal grooves. At least two longitudinally extending rows of a plurality of segmental grooves on the periphery of the tubular body provide liquid communication with the longitudinally extending grooves. The grooves of the one row are longitudinally offset from the grooves of the other row.

U.S. Pat. No. 3,407,817 (Galleher, Jr.) discloses a catheter comprising a tube of elongated configuration adapted to be inserted in a body passageway and having a main bore opening through the end of the tube. A through passage extending longitudinally within the wall of the tube is provided having plug means inserted adjacent one end of the tube to seal the passage. An inflatable cuff encircles the tube at a position near the one end of the tube. The tube passage has communication through the wall of the tube adjacent the plug means with the interior of the inflatable cuff. Cuff inflation means is inserted in the passage near the opposite end of the tube. The inflating means has a pressure release opening. A resilient means is removably secured over the opening. The resilient means in the scaling relation indicates the extent to which the cuff is inflated in response to fluid pressure from the inflating means. The resilient means when removed from the scaling relation simultaneously deflates itself and the cuff.

U.S. Pat. No. 3,590,820 (Nehru) discloses a hollow cylindrical aspirator tip that has radially passages that communicated hollow cylindrical tip with the outer ends of the longitudinal extending slot passages. Specifically, Nehru discloses an aspirator tip comprising a hollow cylindrical member having one closed end. Radially extending primary passages are provided through the aspirator tip adjacent the closed end. Means operably associated with the primary passages for relieving vacuum drawn in the primary passages to prevent damage to mucous membrane in contact with the aspirator tip over the outer end of the primary passages there through on drawing a vacuum through the tip are also included. Longitudinally extending relief passages in the tip communicating are included with the primary passages. Longitudinally extending slots between the exterior surfaces of the tip and the relief passages in the tip are also included to permit drawing of fluid through the slots into the relief passages and subsequently into the interior tip through the primary passages. This type of drain is limited in use and is specifically designed to remove blood and secretion during a surgical incision, whereby the tip is connected to a high vacuum source.

U.S. Pat. No. 3,599,641 (Sheridan) discloses a multilumen catheter having a proximal end, a distal end adapted for insertion in the body of a patient, and a principal channel connecting the distal end with the proximal end for transport of fluid. A secondary channel of smaller size than the principal channel is provided, An opening through the sidewall of the catheter adjacent the proximal end provides fluid flow across to the secondary channel and a connector tube of smaller outside diameter than the catheter fixed at one end to the opening. A combination connector channel closure system for the catheter comprises a first connector member having an enlarged central body portion. A male connector portion on one end and a female portion at the opposite end into which the proximal end of the catheter fixed is also provided. A second connector member of similar configuration to the first connector member is fixed at the female portion to the free end of the connector tube. A short section of flexible plastic tubing is fitted at one end over the male connector portion of the first connector member and is fitted at the other end over the male connector portion of the second connector member. The combination of short tubing and connector members forms a resealable seal against entrance of material into the catheter and the connector tube.

U.S. Pat. No. 3,630,206 (Gingold) discloses a bladder catheter for males having an elongated flexible core element having first and second end portions and an outer surface provided with one or more grooves extending along the core element at the first end portion of the core element for being received and retained within the bladder of a subject to be treated. A flexible tubular member within an opening is slidably received about the core element. After the element with its tubular member about it are inserted into the urethra of the subject with the first end portion of the core element received and retained within the bladder, the tubular member is partially withdrawn from about the core element to an extent allowing the urethra to be flushed by the draining urine while still remaining in position over the second end portion of core element to receive the urine into the tubular member for external disposal. This type of drain is limited in use and is specifically designed to flush the urethra, is not for use in post-surgical drainage, and is always exposed to infection.

U.S. Pat. No. 3,860,008 (Miner et al.) discloses a surgical drain comprising a series of rods lying on two horizontal planes. The rods of one plane are staggered in relation to the rods on the other plane. The rods on the same plane are in spaced relation to each other and the rods on the plane are connected to adjacent rods on the other plane by a web. The drain is adapted to be torn along a web on a line substantially parallel to a rod and adjacent rods are in acute angular relation to each other. This type of drain has a limit of use and is specifically design to the atmosphere, rather than to an outflow tube and being exposed to infection.

U.S. Pat. No. 4,398,910 (Blake et al.) discloses a wound drain catheter for draining fluid form, or supplying medication to, a closed, deep wound having a drain. The drain comprises a core portion having a longitudinal axis. Plural strut portions are provided extending outwardly from the core portion. Overhang portions, connected to the outward ends of the strut portions, respectively, cooperate with the strut portions to form longitudinal lumens. The overhang portions cooperate with each other to form, on the outer surface of the drain, the segments of a segmented, closed curve. The gaps between the segments provide plural longitudinal grooves for fluid communication between the wound and a respective one of the plural lumens. The grooves are sized to inhibit tissue from growing and debris from passing through. The drain is formed of a material which, when placed in tension between the gripping wound tissue and a force used to withdraw the drain from the wound, will reduce sufficiently in cross section to reduce the gripping force to facilitate withdrawal. The drain has a substantially uniform cross section throughout the portion of its length which is placed in tension during such removal to provide means for reducing stress risers and thus preventing breakage. A flexible outflow tube has a smooth exterior for sealing to surface tissue at the point of exit from a patient's body. Means conforming to the segmented, closed curve, for connecting the outflow tube to the drain are also provided.

U.S. Pat. No. 4,445,897 (Ekbladh et al.) discloses a catheter for post surgical drainage of a wound comprising a flexible tube having a distil end and a proximal end. The catheter has a centrally arranged inner lumen that extends longitudinally. The catheter is adapted to be connected at its proximal end to a suction means for withdrawing drainage through the lumen and is adapted for its distal end to be implanted in the wound area to be drained. In the catheter, there is provided at least one longitudinal slot opening in the surface of the distal end of the catheter which connects to a second longitudinal lumen which is at least as long as the slot opening and has a maximum width which is larger than the width of the slot opening. There is further a plurality of through openings extending between the base of the second lumen into the first lumen, whereby drainage can pass from the wound area to the second lumen then into the first lumen.

U.S. Pat. No. 4,465,481 (Blake) discloses an elongate catheter of one piece construction for draining fluid from or supplying fluid to an environment comprising a drain segment of substantially constant cross section throughout its length having plural elongate fluid openings in the form of grooves extending throughout the length of the sidewall. The openings are spaced circumferentially from one another. A second transition segment is provided with closed sidewalls in fluid communication with the elongate openings of the drain segment having an perimeter size, in cross section, substantially the same as that of the drain segment, but having an interior cross section different from that of the drain segment.

U.S. Pat. No. 5,549,579 (Batdorf et al.) discloses a drainage tube having a proximal end and a distal end including an implantable portion adapted for implantation beneath the skin of a patient. The implantable portion has a length and comprising in combination: (a) a hollow tubular collecting portion having a first length, a first outer surface and a first inner surface having struts projecting inward therefrom coextensive with the first length, the first outer surface presenting a uniform first cross-sectional profile along the first length and wherein the first cross-sectional profile has a greatest dimension; and (b) a hollow tubular extension portion having a second length and a second outer surface having a substantially uniform second cross-sectional profile coextensive with the second length, the second cross-sectional profile having a greatest dimension which is less than the greatest dimension of the first cross-sectional profile; and (c) a hollow transition portion therebetween, the transition portion providing an integral connection between the proximal end of the collecting portion and the distal end of the extension portion, the transition portion providing a gradual transition between the first cross-sectional profile and the second cross-sectional profile; the improvement wherein the greatest dimension of the first cross-sectional profile and the greatest dimension of the second cross-sectional profile of the implantable portion of the drainage tube progressively decreases along the length of the implantable portion in the direction of the proximal end of the drain, and wherein the implantable portion is of unitary construction.

U.S. Pat. No. 6,099,513 (Spehalski) discloses a wound drain device for implantation into and for drainage of fluid from a wound of a patient. The device comprises an elongated annular outer wall defining an exterior surface. An elongated central core defining at least one longitudinal axis is provided and is disposed within and spaced radially inwardly from the outer wall. A plurality of elongated radial inner walls is disposed within the outer wall and extends along, outwardly from, and circumferentially spaced about the longitudinal axis. The inner walls further extend between and connect to the central core and the outer wall such that the inner walls together with the outer wall form a plurality of elongated enclosed lumens for draining fluids from the wound. The lumens circumferentially are spaced from one another about and extend along the longitudinal axis such that the inner walls are disposed between the lumens. Each of the inner walls has an elongated open duct defined and extend along the longitudinal axis such that each of the ducts is in a respective one of the inner walls disposed between the lumens. Each of the ducts is formed by an interior base surface defined in the respective one inner wall adjacent to the central core and by a pair of opposing interior side surfaces defined in the respective one inner wall so as to extend from the interior base surface to the exterior surface of the outer wall and define an elongated entrance to the duct through the outer wall to permit fluid flow from the wound exteriorly of the outer wall through the entrance and into the duct. Each of the ducts has a maximum width between the opposing interior side surfaces which is substantially smaller than a maximum width of each of the lumens between the inner walls. This type of drain has limit of use and is specifically design to the atmosphere, rather than to an outflow tube and always exposed to infection causing organism. This type of drain can be easily clogged in the entrance passage area and is closed the drain communication at the entirely lumen (slot) length.

IN THE FIGURES

FIG. 5 is a lateral cross-sectional view of the drain catheter shown in FIG. 4.

FIG. 6 is a longitudinal cross-sectional view of the drain catheter shown in FIG. 4.

FIG. 7 is a lateral cross-sectional view of the drain catheter shown in FIG. 4 in relationship to a wound. The shape of the drain catheter is shown when the pressure in the hollow core is at one atmosphere.

FIG. 8 is a lateral cross-sectional view of the drain catheter shown in FIG. 7 in relationship to a wound. The shape of the drain catheter is shown when the pressure in the hollow core is increased above one atmosphere.

FIG. 9 is a lateral cross-sectional view of the drain catheter shown in FIG. 8 in relationship to a wound. The shape of the drain catheter is shown when the pressure in the hollow core is at maximum pressure.

SUMMARY OF THE INVENTION

Figure 1:
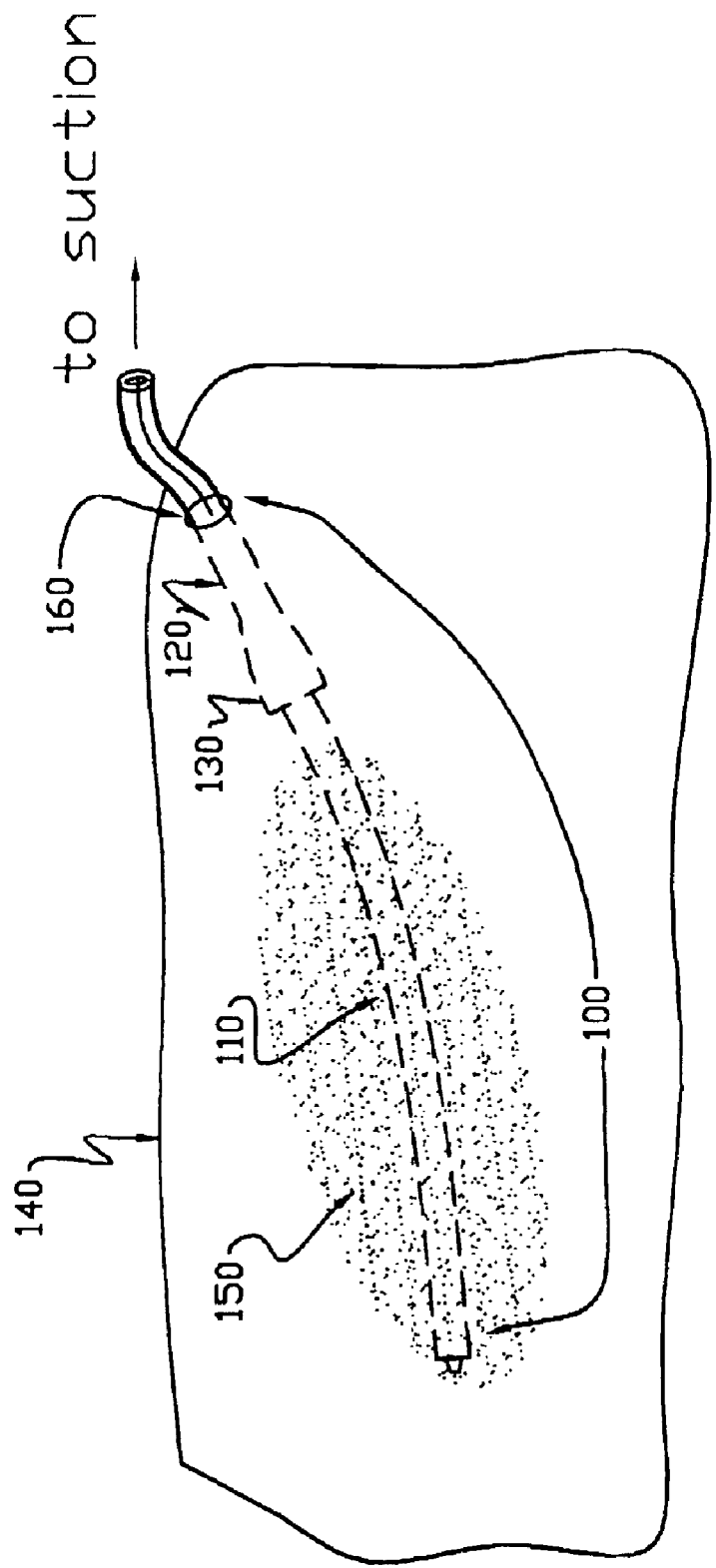
FIG. 1 is a schematic drawing of a wound drain catheter of the present invention placed in a closed, deep wound showing the drain portion and part of the outflow tube in the body of the patient.

The present invention pertains to a wound drain catheter for draining fluid from, or supplying medication to, a wound in a patient comprising:

(A) a drain comprising:
  (a) a hollow core having a longitudinal axis;
  (b) plural struts extending outwardly from the hollow core and being closed to the hollow core; and
  (c) plural overhangs connected to the outward ends of the struts, respectively, the overhangs cooperating with the struts to form plural longitudinal lumens, the overhangs cooperating with each other to form, on the outer surface of the drain, segments of a segmented, closed curve with gaps between the segments providing plural longitudinal grooves for fluid communication between the wound and a respective lumen, the grooves sized to inhibit tissue from growing therein and debris from passing therethrough;

(B) a flexible outflow tube having a smooth exterior for sealing to surface tissue at the point of exit from the body of a patient; and (C) means conforming to the segmented, closed curve for connecting the drain to the flexible outflow tube.

The present invention also pertains to a method for draining fluid from, or supplying medication to, a wound in a patient comprising:

(1) providing a drain catheter having a flexible outflow tube;

(2) placing the drain catheter and the flexible outflow tube in the wound of a patient;

(3) closing the wound to seal the wound from the atmosphere;

(4) connecting the flexible outflow tube to a reservoir; and (5) removing the drain catheter from the wound by applying a tensile force;

wherein the drain catheter comprises:

(A) a drain comprising:
  (a) a hollow core having a longitudinal axis;
  (b) plural struts extending outwardly from the hollow core and being closed to the hollow core; and
  (c) plural overhangs connected to the outward ends of the struts, respectively, the overhangs cooperating with the struts to form plural longitudinal lumens, the overhangs cooperating with each other to form, on the outer surface of the drain, segments of a segmented, closed curve with gaps between the segments providing plural longitudinal grooves for fluid communication between the wound and a respective lumen, the grooves sized to inhibit tissue from growing therein and debris from passing therethrough;

(B) a flexible outflow tube having a smooth exterior for sealing to surface tissue at the point of exit from the body of a patient; and (C) means conforming to the segmented, closed curve for connecting the drain to the flexible outflow tube.

DETAILED DESCRIPTION OF THE INVENTION

The present invention comprises a wound drain catheter for draining fluid from, or supplying medication to, a wound in a patient. The drain of the present invention provides an increased tissue contact drainage area and an increased lumenal flow drainage area compared to prior art drains. Further, the specific configuration of this wound drain catheter provides an increased drain body cross-sectional area and eliminates weak points in the drain body. This configuration makes the wound drain catheter of the present invention stronger than comparably sized drains and therefore less likely to break during removal. Moreover, the present drain configuration reduces the risk that tissue growth will inhibit removal of the drain. Thus, the drain provides safety, reliability, and effectiveness not found in prior art drains.

The wound drain catheters of the present invention are fluted and comprise a hollow central core with radially projecting strut portions. The radial strut portions may or may not be of equal size and may or may not be spaced at equal angles relative to each other. An overhang portion extends from the end of each strut portion to form T-shaped members. These overhang portions form the periphery of the wound drain. The overhang portions and strut portions together form channels or lumens which extend throughout the length of the wound drain catheter. When viewed from a lateral cross-sectional angle, the overhang portions form a segmented circle having gaps between adjacent overhang portions. These gaps extend longitudinally throughout the length of the drain and form grooves which permit fluid entry into the lumens. The grooves that do not have direct contact tissue may have a width of about 0 to 0.3 times the diameter of the drain.

The hollow tube portion may be inflated or deflated to accommodate the draining process. This is especially important during removal of the wound drain catheter. Inflating the wound drain catheter prior to removing it with a strong pulling force counters the tendency of the wound drain catheter to decrease in diameter when pulled and thereby minimizes pinching and the subsequent trapping of any tissue that has grown into the drain during drain removal.

The hollow core of the wound drain catheter may be filled with biocompatible liquids or gases or combinations of both. The hollow core of the wound drain catheter may also be filled with one or more biocompatible springs. The filler material can be preset inside the hollow core for atmospheric pressure, for example, and then a doctor can change pressure inside the hollow core for higher or lower pressure, or pulsation. When the pressure in the hollow core is increased, the groves are opened and the effectiveness of the drain process is better than at ambient pressure. In addition, when the pressure is increased inside the hollow core, the groves are opened such that embedded tissue slides out from the catheter grove structure without ripping the tissue. As the doctor removes the drain, the pulling force causes the wound drain catheter to "neck down", or reduce in cross-sectional area, along its length, thereby relieving the gripping force of the tissue and permitting the drain to be more easily removed. The different levels of pressure in the hollow core help control the effectiveness of the drain process and eliminates tissue trauma during removal of the drain catheter from the patient.

The overhang portions form the periphery of the wound drain and may optionally have spaced apertures on the outward ends of the overhang portions. The spaced apertures may or may not be of equal size and may or may not be spaced at equal distances relative to each other. The spaced apertures provide additional fluid entry into the lumens.

One or more constraint sutures or guide wires may optionally be included inside the hollow core portion, the lumen, or even in the solid strut portion or overhang portion. A first end of the constraint suture or guide wire may be attached to a proximal end of the drain and a second end of the constraint suture may be attached to a distal end of the drain or to the flexible outflow tube. In this way, the constraint suture or guide wire provides additional cross-sectional strength and prevents breakage of the drain during removal. The use of constraint or reinforcing guide wires also permits the use of a smaller diameter and more pliable drain system with thinner walls without decreasing the strength of the catheter. The use of constraint sutures also prevents the wound drain catheter from excessively "necking down". The hollow core with filler or with constrain sutures also makes the drain catheter more pliable and flexible and prevents the catheter from kinking compared to solid core catheters.

The invention will be better understood from the following detailed description of the preferred embodiments taken in conjunction with the Figures, in which like elements are represented by like referenced numerals.

FIG. 1 is a schematic drawing of the wound drain catheter in a preferred embodiment of the present invention. The drain and part of the outflow tube are placed in a closed, deep wound in the body of a patient. In FIG. 1, the wound drain catheter is depicted generally as 100 and is constructed in accordance with a preferred embodiment of the present invention. The wound drain catheter 100 for use in draining fluid from, or supplying medication to, a wound in a patient includes a drain 110 preconnected to a flexible outflow tube 120 via a means 130 connecting the outflow tube 120 to the drain 110. The drain 110 and a small part of the flexible outflow tube 120 are placed in the patient's body 140 with the drain 110 in fluid communication with the wound 150. Preferably, the flexible outflow tube 120 is connected to a sealed, sterilized suction device (not shown) for drawing fluid through the wound drain catheter 100. In addition, it is also preferable that the outflow tube 120 exit the patient's body 140 through an aperture 160 formed in healthy tissue adjacent to the wound 150. Further, the outflow tube 120 should have a smooth exterior to permit the surface tissue surrounding the aperture 160 to seal against the exterior of the tube 120, and thus, prevent air from passing therebetween. Thus, since the drain 110 is open only to the sterile suction device, and not to the atmosphere, the risk of infection is reduced. Preferably, the outflow tube 120 and the drain 110 are connected end-to-end in an abutting relationship. The means conforming (connecting means) the outflow tube 120 to the drain 110 may comprise a collar (not shown).

The wound drain catheters 110 of the present invention are preferably made from a silicone elastomer since silicone is biocompatible, soft, and flexible. Materials such as PVC are less biocompatible and are more rigid and tend to irritate wounds causing discomfort and inhibiting healing. Materials such as natural rubber are rarely used because of toxicity problems.

Figure 2:
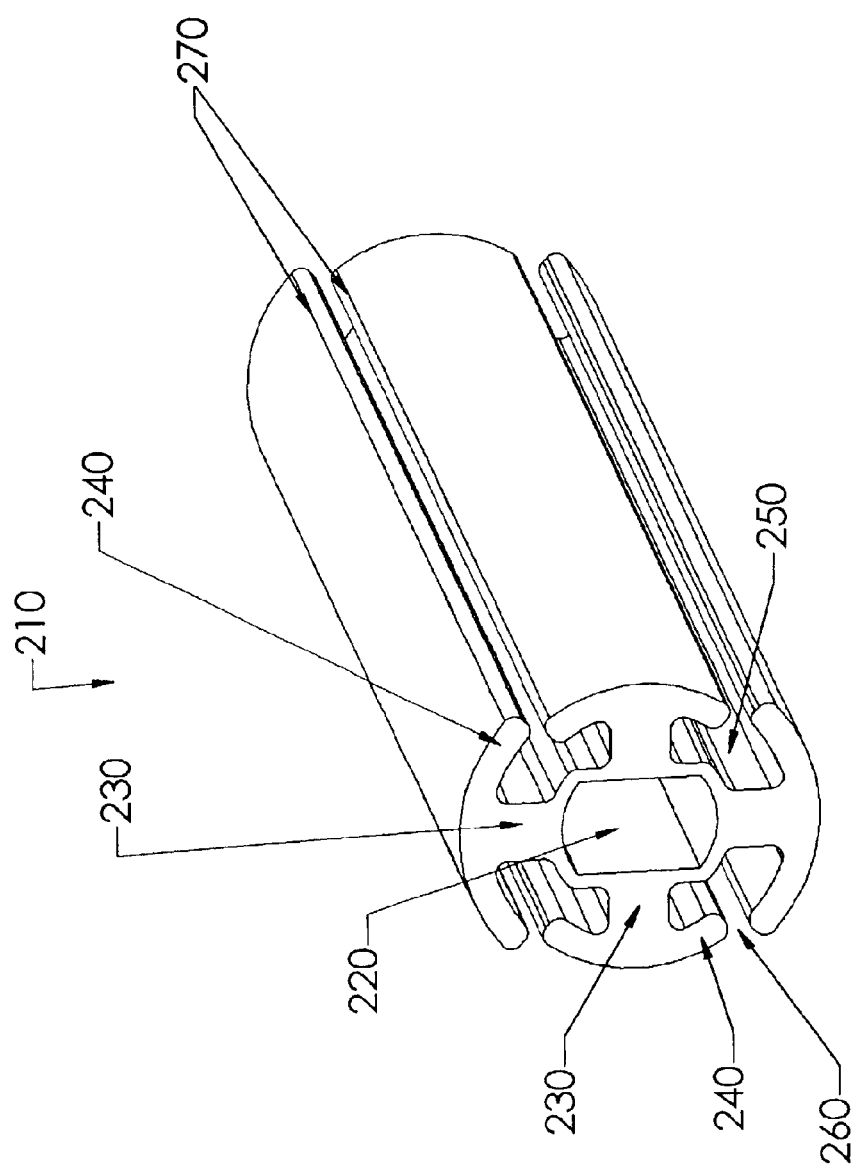
FIG. 2 is a schematic drawing of a first embodiment of the present invention showing a round fluted wound drain catheter with a hollow core portion and four lumens.

FIG. 2 is a schematic drawing of the drain in the wound drain catheter in a preferred embodiment of the present invention. In FIG. 2, the drain is depicted generally as 210 and is constructed in accordance with a preferred embodiment of the present invention. The drain 210 comprises a hollow core portion 220 having a longitudinal axis. Plural strut portions 230 extend outwardly from the hollow core 220. The plural struts 230 are closed to the hollow core portion 220. Plural overhang portions 240 are connected to the outward ends of the strut portions 230, respectively. The overhang portions 240 cooperate with the strut portions 230 to form plural longitudinal lumens 250. The overhang portions 240 cooperate with each other to form, on the outer surface of the drain, the segments of a segmented, closed curve, the gaps 260 between the segments providing plural longitudinal grooves 270 for fluid communication between the wound 150 and the plural lumens 250. The grooves 270 are sized to inhibit tissue from growing therein and debris from passing therethrough. Optionally, the plural strut portions 230 may combine with respective plural overhang portions 240 to form plural T-shaped members which may or may not be the same size.

The hollow core portion 220 may be any shape including round, oval, 3-sided, square, rectangular, 5-sided, and the like, depending upon the ultimate use of the wound drain catheter. The hollow core 220 may be filled with biocompatible liquids or gases or combinations of both. The hollow core 220 may also be filled with one or more biocompatible springs. The drain 210 may have a plurality of strut portions 230 such as two, three, four, or more strut portions 230, extending from the hollow core portion 220. The plural strut portions 230 may or may not project radially from the hollow core portion 220 at equal or unequal angles relative to each other. The drain 210 may be uniform in cross-section throughout its length. The longitudinal grooves 270 may be parallel to the longitudinal axis. The drain 210 may be radially symmetrical. The radially symmetrical drain 210 may have corresponding portions of the drain on each of equiangular, plural radii extending from the central axis, and the corresponding portions are equidistant from the central axis. The drain may have diametrical symmetry. The closed curve may be a circle or may be an oval. Preferably, the closed curve is an oval.

Figure 3:
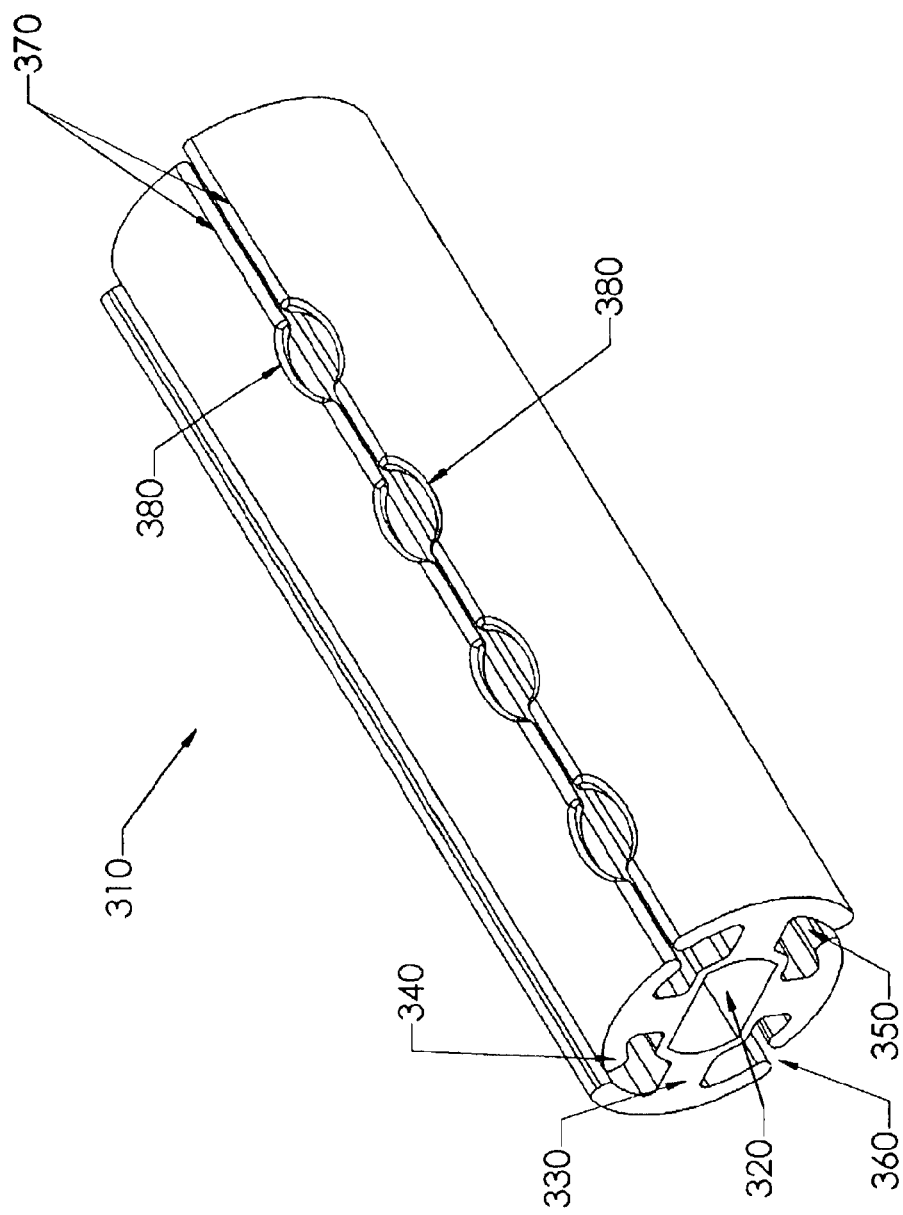
FIG. 3 is another schematic drawing of the drain catheter shown in FIG. 2 illustrating spaced apertures.

FIG. 3 is another schematic drawing of the drain catheter shown in FIG. 2 illustrating spaced apertures. In FIG. 3, the drain is depicted generally as 310 and is constructed in accordance with a preferred embodiment of the present invention. The drain 310 comprises a hollow core portion 320 having a longitudinal axis. Plural strut portions 330 extend outwardly from the hollow core 320 and plural overhang portions 340 are connected to the outward ends of the strut portions 330, respectively. The overhang portions 340 cooperate with the strut portions 330 to form plural longitudinal lumens 350. The overhang portions 340 cooperate with each other to form, on the outer surface of the drain, a segmented, closed curve, the gaps 360 between the segments providing plural longitudinal grooves 370 for fluid communication between the wound and the plural lumens 350. Plural overhang portions 340 have plural spaced apertures 380 on the outward ends thereof. The plural spaced apertures 380 may or may not be evenly spaced. The spaced apertures 380 provide for fluid communication between the wound and the plural lumens 350.

Figure 4:
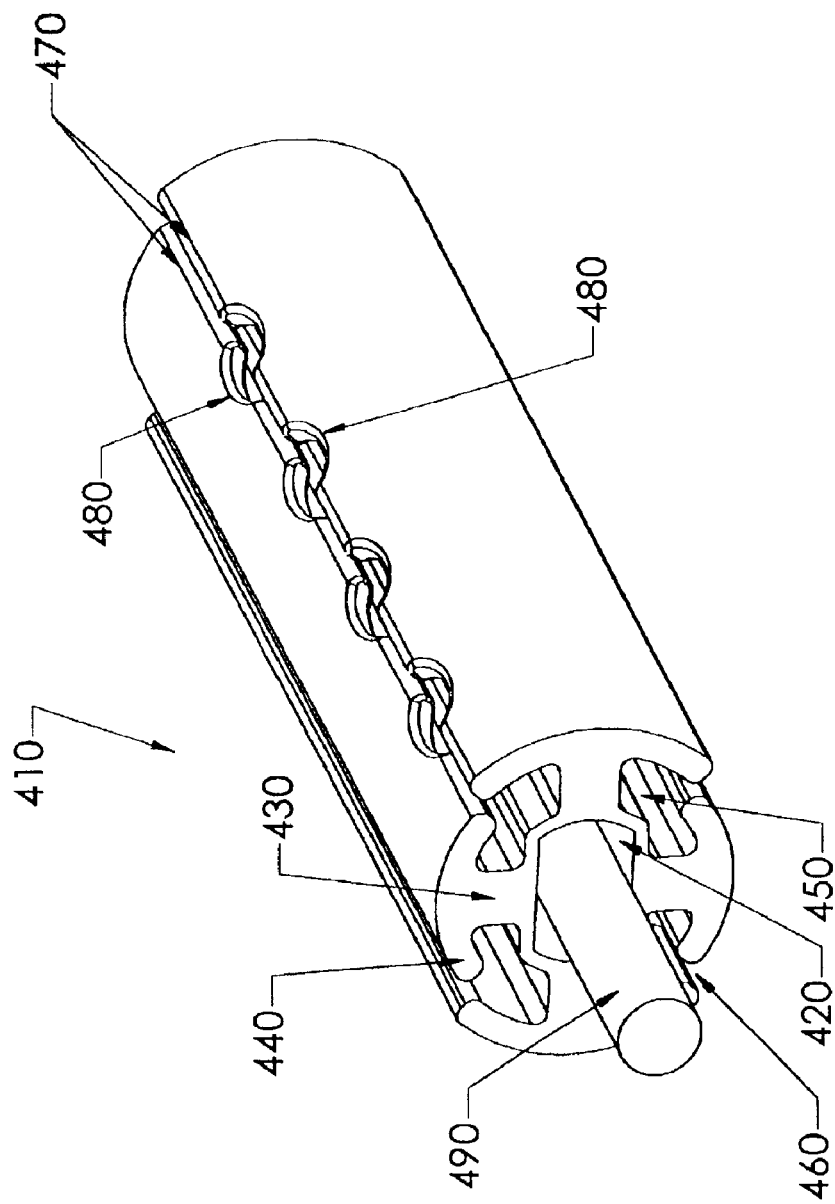
FIG. 4 is another schematic drawing of the drain catheter shown in FIG. 2 illustrating spaced apertures and a constraint suture.

FIG. 4 is another schematic drawing of the drain catheter shown in FIG. 2 illustrating spaced apertures and a constraint suture. In FIG. 4, the drain is depicted generally as 410 and is constructed in accordance with a preferred embodiment of the present invention. The drain 410 comprises a hollow core portion 420 having a longitudinal axis. Plural strut portions 430 extend outwardly from the hollow core 420 and plural overhang portions 440 are connected to the outward ends of the strut portions 430, respectively. The overhang portions 440 cooperate with the strut portions 430 to form plural longitudinal lumens 450. The overhang portions 440 cooperate with each other to form, on the outer surface of the drain, a segmented, closed curve, the gaps 460 between the segments providing plural longitudinal grooves 470 for fluid communication between the wound and the plural lumens 450. Plural overhang portions 440 have plural spaced apertures 480 on the outward ends thereof. One or more constraint sutures or guide wires 490 are present inside the hollow core portion 420. A first end of the constraint suture 490 may be attached to a proximal end of the drain 410 and a second end of the constraint suture 490 may be attached to a distal end of the drain 410 or to the flexible outflow tube. The constraint suture 490 provides additional cross-sectional strength and prevents breakage of the drain 410 during removal. The use of constraint or reinforcing sutures 490 also permits the use of a smaller diameter and more pliable drain system 410 with thinner walls without decreasing the strength of the drain catheter.

FIG. 5 is a lateral cross-sectional view of the drain catheter shown in FIG. 4. In FIG. 5, the drain is depicted generally as 510 and is constructed in accordance with a preferred embodiment of the present invention. The drain 510 comprises a hollow core portion 520 having a longitudinal axis. Plural strut portions 530 extend outwardly from the hollow core 520 and plural overhang portions 540 are connected to the outward ends of the strut portions 530, respectively. The overhang portions 540 cooperate with the strut portions 530 to form plural longitudinal lumens 550. The overhang portions 540 cooperate with each other to form, on the outer surface of the drain, a segmented, closed curve, the gaps 560 between the segments providing plural longitudinal grooves 570 for fluid communication between the wound and the plural lumens 550. Plural overhang portions 540 have plural spaced apertures (not shown) on the outward ends thereof. One or more constraint sutures 590 are present inside the hollow core portion.

FIG. 6 is a longitudinal cross-sectional view of the drain catheter shown in FIG. 4. In FIG. 6, the drain is depicted generally as 610 and is constructed in accordance with a preferred embodiment of the present invention. A constraint suture 690 is present inside the hollow core portion 620. A first end of the constraint suture 690 is attached to a proximal end of the drain 691 via a plug 692. A second end of the constraint suture 690 is attached to a distal end of the drain or to the flexible outflow tube (not shown).

FIG. 7 is a lateral cross-sectional view of the drain catheter shown in FIG. 4 in relationship to a wound 150. In FIG. 7, the drain is depicted generally as 710 and is constructed in accordance with a preferred embodiment of the present invention. The drain 710 comprises a rectangular hollow core portion 720 with a constraint suture 790 present inside the hollow core portion 720. Plural overhang portions 740 are connected to the outward ends of the strut portions 730, respectively, to form large T-shaped members 741 and small T-shaped members 742. Large T-shaped members 741 are connected to a relatively small cross sectional area of rectangular hollow core portion 720 and small T-shaped members 742 are connected to a relatively large cross sectional area of rectangular hollow core portion 720. The shape of the drain 710 in relationship to the wound 150 is shown when the pressure in the rectangular hollow core 720 is one atmosphere.

FIG. 8 is a lateral cross-sectional view of the drain catheter shown in FIG. 7 in relationship to a wound 150. In FIG. 8, the drain is depicted generally as 810 and is constructed in accordance with a preferred embodiment of the present invention. The shape of the drain catheter 810 in relationship to the wound 150 is shown when the pressure in the hollow core 820 is increased above one atmosphere. Because large T-shaped members 841 are connected to a relatively small cross sectional area of rectangular hollow core portion 820 and small T-shaped members 842 are connected to a relatively large cross sectional area of rectangular hollow core portion 820, small T-shaped members 842 expand to meet large T-shaped members 841 as the pressure in the hollow core 820 is increased above one atmosphere.

FIG. 9 is a lateral cross-sectional view of the drain catheter shown in FIG. 7 in relationship to a wound 150. In FIG. 9, the drain is depicted generally as 910 and is constructed in accordance with a preferred embodiment of the present invention. The shape of the drain catheter 910 in relationship to the wound 150 is shown when the pressure in the hollow core is at maximum pressure. Because large T-shaped members 941 are connected to a relatively small cross sectional area of rectangular hollow core portion 920 and small T-shaped members 942 are connected to a relatively large cross sectional area of rectangular hollow core portion 920, small T-shaped members 942 expand past large T-shaped members 941 to form reversed gaps as the pressure in the hollow core 920 is increased above one atmosphere.

This ability to change the size of the gaps in the wound drain catheter of the present invention helps to keep the drain efficient, relieves the gripping force on the tissue, and makes the wound drain catheter easier to remove from the patient, and reduces the risk of damage to the tissues surrounding the wound. The hollow tube portion may be inflated or deflated to accommodate the draining process. This is especially important during removal of the wound drain catheter. Deflating the wound drain catheter prior to removing it with a strong pulling force counters the tendency of the wound drain catheter to decrease in diameter when pulled and thereby minimizes pinching and the subsequent trapping of any tissue that has grown into the drain during drain removal. The hollow core of the wound drain catheter may be filled with biocompatible liquids or gases or combinations of both. The hollow core of the wound drain catheter may also be filled with one or more biocompatible springs. The different levels of pressure in the hollow core helps control the effectiveness of the drain process and eliminates tissue trauma during removal of the drain catheter from the patient.

Figure 10:
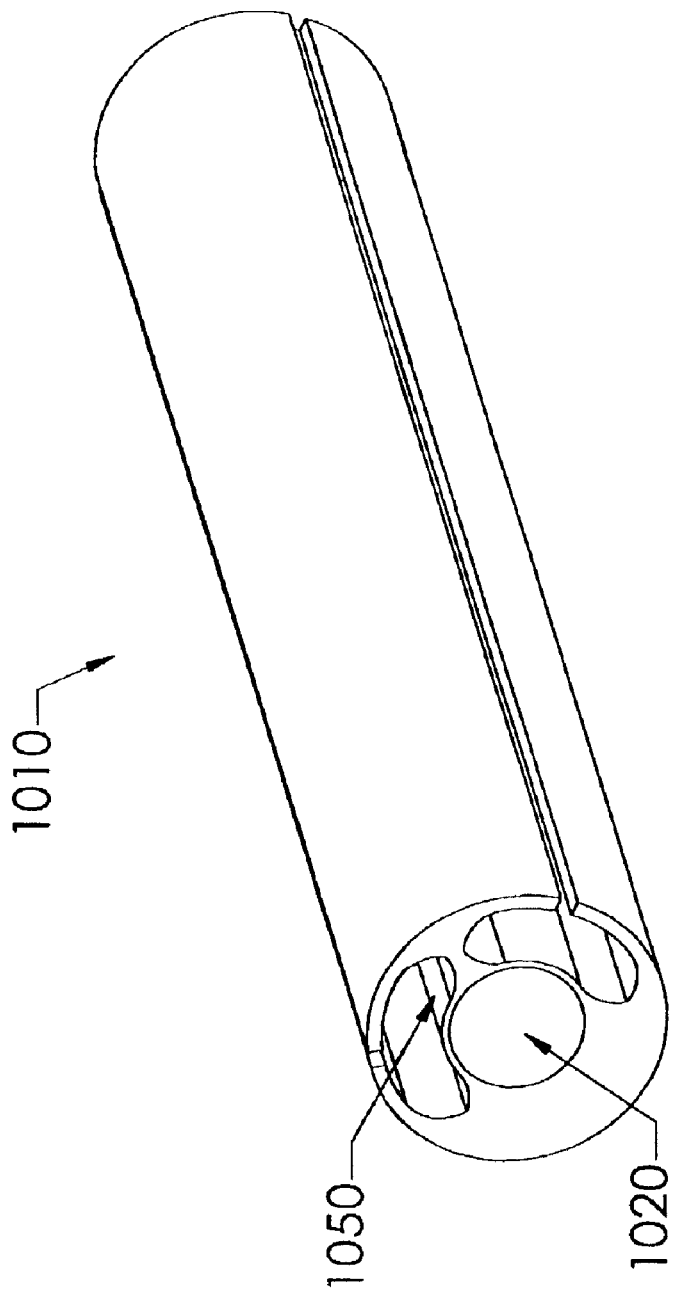
FIG. 10 is a schematic drawing of a round fluted wound drain catheter with a hollow core portion and two lumens.

FIG. 10 is a schematic drawing of a round fluted wound drain catheter 1010 with a hollow core portion 1020 and two lumens 1050.

Figure 11:
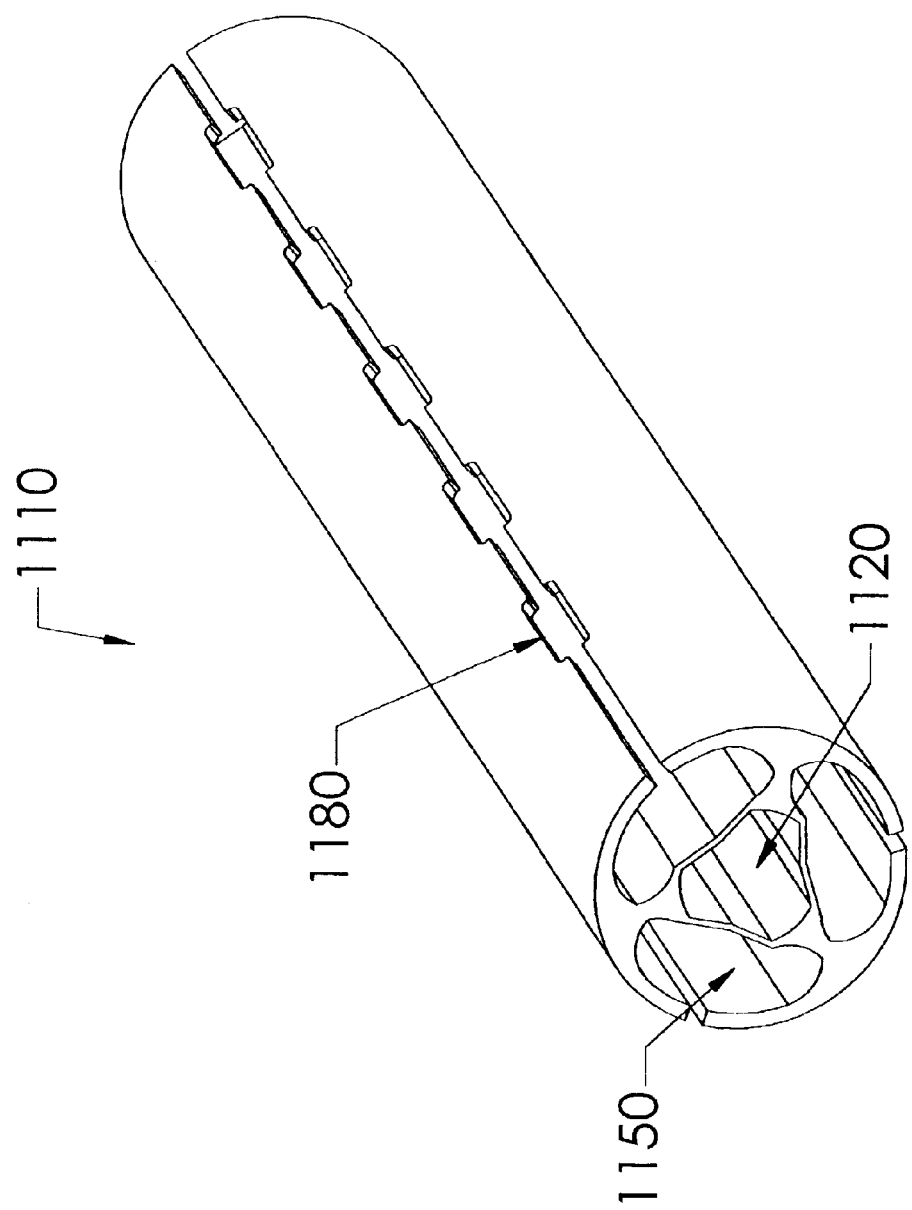
FIG. 11 is a schematic drawing of a round fluted wound drain catheter with a hollow core portion, three lumens, and spaced apertures.

FIG. 11 is a schematic drawing of a round fluted wound drain catheter 1110 with a hollow core portion 1120, three lumens 1150, and spaced apertures 1180.

The drain catheter may further incorporate a radiopaque material so that the drain catheter is opaque to various forms of radiation, such as X-rays. In this way, the location of the drain catheter may be determined in the body of a patient.

Several techniques may be employed to insert a wound drain catheter into a patient. For example, a surgeon may simply place the drain portion and a small part of the outflow tube portion in the wound, close the incision, and suture around the outflow tube portion. This technique is somewhat unsatisfactory since it is difficult to completely seal the area around the outflow tube by suturing, and thus, the wound may become infected. A more satisfactory technique is to pass a trocar, preattached to the end of the outflow tube, through healthy tissue by entering the patient at a point within the wound and exiting at a point adjacent to the wound. The surgeon may then pull the outflow tube portion through the tissue with the trocar until the catheter is properly positioned, with the drain in the wound. Since the outflow tube exits the body at a point adjacent the wound, the wound can be completely closed by suturing thereby reducing the risk of infection.

In another embodiment, the present invention pertains to a method for draining fluid from, or supplying medication to, a wound in a patient comprising:

(1) providing a drain catheter having a flexible outflow tube;

(2) placing the drain catheter and the flexible outflow tube in the wound of a patient;

(3) closing the wound to seal the wound from the atmosphere;

(4) connecting the flexible outflow tube to a reservoir; and (5) removing the drain catheter from the wound by applying a tensile force;

wherein the drain catheter comprises:

(A) a drain comprising:
  (a) a hollow core having a longitudinal axis;
  (b) plural struts extending outwardly from the hollow core and being closed to the hollow core; and
  (c) plural overhangs connected to the outward ends of the struts, respectively, the overhangs cooperating with the struts to form plural longitudinal lumens, the overhangs cooperating with each other to form, on the outer surface of the drain, segments of a segmented, closed curve with gaps between the segments providing plural longitudinal grooves for fluid communication between the wound and a respective lumen, the grooves sized to inhibit tissue from growing therein and debris from passing therethrough;

(B) a flexible outflow tube having a smooth exterior for sealing to surface tissue at the point of exit from the body of a patient; and (C) means conforming to the segmented, closed curve for connecting the drain to the flexible outflow tube.

The invention being thus described, it will be obvious that the same may be varied in many ways. Such variations are not to be regarded as a departure from the spirit and scope of the invention and all such modifications are intended to be included within the scope of the following claims.

I claim:

1. A wound drain catheter for draining fluid from, or supplying medication to, a wound in a patient comprising:
   (A) a drain comprising:
     (a) a hollow core having a longitudinal axis and a continuous closed periphery, said hollow core including at least one interior lumen sealed at a proximal end thereof;
     (b) plural struts extending outwardly from the periphery of the hollow core and being closed to the at least one interior lumen of the hollow core; and
     (c) plural overhangs connected to the outward ends of the struts, respectively, the overhangs cooperating with the struts and the periphery of the hollow core to form plural longitudinal exterior lumens isolated from the at least one interior lumen of the hollow core, the overhangs cooperating with each other to form, on the outer surface of the drain, segments of a segmented, closed curve with gaps between the segments providing plural longitudinal grooves for fluid communication between the wound and a respective exterior lumen, the grooves being sized to inhibit tissue from growing therein and debris from passing therethrough;
   (B) a flexible outflow tube having a smooth exterior for sealing to surface tissue at the point of exit from the body of a patient; and
   (C) means conforming to the segmented, closed curve for connecting the drain to the flexible outflow tube.

2. The wound drain catheter according to claim 1, wherein the at least one interior lumen of the hollow core is round.

3. The wound drain catheter according to claim 1, wherein the at least one interior lumen of the hollow core is rectangular.

4. The wound drain catheter according to claim 1, further comprising a constraint suture or guide wire in a selected one of the at least one interior lumen of the hollow core.

5. The wound drain catheter according to claim 4, wherein a first end of the constraint suture is attached to the proximal end of the drain and a second end of the constraint suture is attached to a distal end of the drain or to the flexible outflow tube.

6. The wound drain catheter according to claim 1, wherein the plural struts combine with respective plural overhangs to form plural T-shaped members.

7. The wound drain catheter according to claim 6, wherein the plural T-shaped members are the same size.

8. The wound drain catheter according to claim 6, wherein the plural T-shaped members are not the same size and the smaller plural T-shaped members are connected to a larger cross sectional area of the hollow core than the larger T-shaped members.

9. The wound drain catheter according to claim 1, wherein the overhangs have plural spaced apertures on the outward ends thereof.

10. The wound drain catheter according to claim 1, wherein the drain has at least four struts extending from the periphery of the hollow core.

11. The wound drain catheter according to claim 1, wherein the plural struts project radially from the periphery of the hollow core at equal angles relative to each other.

12. The wound drain catheter according to claim 1, wherein the drain is uniform in cross-section throughout its length.

13. The wound drain catheter according to claim 1, wherein the longitudinal grooves are parallel to the longitudinal axis of the hollow core.

14. The wound drain catheter according to claim 1, wherein the drain is radially symmetrical.

15. The wound drain catheter according to claim 1, wherein the drain catheter comprises a radiopaque material.

16. The wound drain catheter according to claim 1, wherein the hollow core further comprises a biocompatible filler.

17. The wound drain catheter according to claim 1, wherein the hollow core further comprises a biocompatible spring.

18. The wound drain catheter according to claim 1, further comprising a constraint suture or guide wire in the solid strut or overhang.

19. The wound drain catheter according to claim 5, wherein the first end of the constraint suture is attached to the proximal end of the drain by a plug which functions to seal the proximal end of the selected one of the at least one interior lumen of the hollow core.

20. A method for draining fluid from, or supplying medication to, a wound in a patient comprising the steps of:

(1) providing a drain catheter having a flexible outflow tube;

(2) placing the drain catheter and the flexible outflow tube in the wound of a patient;

(3) closing the wound to seal the wound from the atmosphere;

(4) connecting the flexible outflow tube to a reservoir; and (5) removing the drain catheter from the wound by applying a tensile force;

wherein the drain catheter comprises:

(A) a drain comprising:
   (a) a hollow core having a longitudinal axis and a continuous closed periphery, said hollow core including at least one interior lumen sealed at a proximal end thereof;
   (b) plural struts extending outwardly from the periphery of the hollow core and being closed to the at least one interior lumen of the hollow core; and
   (c) plural overhangs connected to the outward ends of the struts, respectively, the overhangs cooperating with the struts and the periphery of the hollow core to form plural longitudinal exterior lumens isolated from the at least one interior lumen of the hollow core, the overhangs cooperating with each other to form, on the outer surface of the drain, segments of a segmented, closed curve with gaps between the segments providing plural longitudinal grooves for fluid communication between the wound and a respective exterior lumen, the grooves being sized to inhibit tissue from growing therein and debris from passing there through;

(B) a flexible outflow tube having a smooth exterior for sealing to surface tissue at the point of exit from the body of a patient; and (C) means conforming to the segmented, closed curve for connecting the drain to the flexible outflow tube.

* * * * *